United States Patent [19]
Hahn et al.

[11] Patent Number: 5,849,550
[45] Date of Patent: *Dec. 15, 1998

[54] PREPARATION OF LYSOCELLIN BEADS BY FERMENTATION

[75] Inventors: Donald R. Hahn, Mundelein, Ill.; James R. McMullen; Vikram P. Mehrotra, both of Terre Haute, Ind.

[73] Assignee: Mallinckrodt Veterinary, Inc., Mundelein, Ill.

[*] Notice: This patent issued on a continued prosecution application filed under 37 CFR 1.53(d), and is subject to the twenty year patent term provisions of 35 U.S.C. 154(a)(2).

[21] Appl. No.: 497,397

[22] Filed: Jun. 30, 1995

[51] Int. Cl.⁶ .............................. C12P 17/16; C12P 17/18
[52] U.S. Cl. .......................... 435/118; 435/119; 435/244; 549/414
[58] Field of Search ..................................... 435/118, 119, 435/244; 549/414

[56] References Cited

U.S. PATENT DOCUMENTS

| | | |
|---|---|---|
| 4,033,823 | 7/1977 | Liu et al. . |
| 4,478,935 | 10/1984 | Williams et al. . |
| 5,041,374 | 8/1991 | Chu et al. ................. 435/118 |
| 5,047,338 | 9/1991 | Miescher . |
| 5,047,339 | 9/1991 | Mehrotra ................. 435/118 |

*Primary Examiner*—Irene Marx
*Attorney, Agent, or Firm*—Lerner, David, Littenberg, Krumholz & Mentlik

[57] ABSTRACT

A method for producing lysocellin in bead form comprises:

(a) cultivating a lysocellin-producing microorganism in an aqueous nutrient-containing fermentation broth under lysocellin-producing conditions;

(b) adding a base or inorganic phosphate to the fermentation broth within about the first 24 hours of the beginning of the fermentation in an amount sufficient to ensure that the lysocellin is produced in the form of a cation salt of lysocellin;

(c) providing a lipid to the fermentation broth such that the lipid is present in the broth in a sufficient amount to form discrete beads with the lysocellin in the fermentation broth; and (d) separating the beads from the broth.

16 Claims, No Drawings

PREPARATION OF LYSOCELLIN BEADS BY FERMENTATION

BACKGROUND OF THE INVENTION

1. Field of the Invention

The present invention relates to the production of lysocellin in bead form.

2. Description of the Background Art

Lysocellin is a polyether antibiotic which is a fermentation product of *Streptomyces cacaoi* var. asoensis (Ebata et al., *J. Antibiotics* 28:118–121, 1975). Suitable liquid fermentation media generally are aqueous dispersions containing sources of assimilable nitrogen and carbon as are known in the art. The fermentation media also can contain a variety of optional ingredients, if desired, such as pH adjustment agents, buffers, trace minerals, antifoam agents and the like.

Known methods for recovering lysocellin and other polyether antibiotics from fermentation broths generally have involved complicated and multi-stage solvent extractions and related filtration, chromatography, concentration and crystallization operations. For example, the procedure used to isolate and purify lysocellin described by Ebata et al. employed acetone, n-butanol and methanol. U.S. Pat. No. 4,033,823 describes an extraction process involving ethylacetate, acetonitrile, hexane and methanol for recovering lysocellin. U.S. Pat. No. 4,478,935 describes various purified manganese-containing antibiotic complexes extracted from the dried biomass using suitable organic solvents followed by crystallization or precipitation of the complexes.

All of these methods involved a number of steps, and accordingly were both costly and time-consuming. In U.S. Pat. No. 5,047,338, Miescher disclosed and claimed a method for obtaining lysocellin and other polyether antibiotics in agglomerate or bead form, which could be recovered from the fermentation broth by means of a simple screening step. The patent teaches providing the fermentation broth with a physiologically-acceptable lipid. As the fermentation proceeds, lysocellin accumulates in the broth and will be attracted to the lipid due to the lipophilic nature and water insolubility of the lysocellin. If, at the end of the fermentation, sufficient lipid is present in the broth, agglomerates, or beads, will form between the lipid and the lysocellin. The formation of beads simplifies the recovery procedures, but the method has not always consistently produced the polyether antibiotic in bead form. The level of oil in the fermentor must be carefully monitored. If the level of residual oil in the fermentor becomes too high, unrecoverable globs of oil and lysocellin can result. Conversely, if oil levels are too low, beads do not form. Even if the oil level is correct, bead formation is unpredictable as factors other than oil level appear to control or influence bead formation, as discussed below.

Accordingly, it is an object of the present invention to provide a method for producing lysocellin, wherein the lysocellin is consistently produced in high yields and in bead form, which is easily recoverable from the fermentation broth. Other objects of the invention will become apparent from the following description of the invention.

SUMMARY OF THE INVENTION

The present invention is directed to a method for producing lysocellin in bead form which comprises:

(a) cultivating a lysocellin-producing microorganism in an aqueous nutrient-containing fermentation broth under lysocellin-producing conditions;

(b) adding a base or inorganic phosphate to the fermentation broth within about the first 24 hours of the beginning of the fermentation in an amount sufficient to ensure that the lysocellin is produced in the form of a cation salt of lysocellin;

(c) providing a lipid to the fermentation broth such that the lipid is present in the broth in a sufficient amount to form discrete beads with the lysocellin in the fermentation broth; and (d) separating the lysocellin-containing beads from the broth.

DETAILED DESCRIPTION OF THE INVENTION

U.S. Pat. No. 5,047,338 teaches the production of lysocellin in bead form by adding a combination of glycerides and free fatty acids to a fermentation broth comprising a lysocellin-producing microorganism. The patent provides simply that the pH of the fermentation broth desirably is adjusted to be within the range of about 6.5 to 7.5 and that beads are formed by controlling the concentration of the glycerides and free fatty acids in the broth. It now surprisingly has been discovered that formation of lysocellin in bead form can be much more carefully controlled by ensuring that the lysocellin is produced in the form of a cation salt.

Formation of the lysocellin in this form requires more than simply maintaining the pH of the fermentation broth at a neutral pH, as the standard components of broth typically do not provide a sufficient amount of a cation to enable the formation of lysocellin in the form of a cation salt. Therefore, the cation concentration in the medium must be adjusted to catalyze the formation of the cation salt of lysocellin, which in the presence of oil forms beads. It has been found that the oil acts as a binding agent with the cation salt of lysocellin and does not by itself catalyze bead formation as previously had been taught. Cation concentration in the medium is increased by the addition of a base or inorganic ion salt as a buffering agent.

The lysocellin salt to be formed can comprise a sodium, potassium, ammonium, calcium or other divalent metal salt. Sodium salts are preferred. Thus, a few examples of suitable bases or inorganic salts which can be added to the fermentation broth include sodium hydroxide, mono- and/or di-basic sodium phosphates, potassium hydroxide, mono- and/or di-basic potassium phosphates, ammonium hydroxide and/or mono- and di-basic ammonium phosphates.

The base or inorganic salt is added to the culture medium in an amount sufficient to raise the concentration of cation in the medium to a minimum of 25 mM in about the first 24 hours of the fermentation. Preferably, the base or inorganic salt is added to the medium to raise the concentration of the cation to be within the range of about 25 mM to about 50 mM. This can be accomplished using any of several approaches. For example, the pH set point in the fermentor can be raised to at least pH 7.2, preferably within the range of about 7.2 to about 7.6. The volume of base added to equilibrate the fermentor broth to this pH and then maintain the pH within the range of about 7.2 to about 7.6 thereafter is sufficient to raise the ion concentration in the broth to have the lysocellin produced in the salt form. The salt form of lysocellin is dependent on the ion present in the added base (see Example 1, below).

Alternatively, lysocellin will be produced in salt form when mono- and di-basic phosphates, such as sodium or potassium phosphates, are added to an amount comprising at least 0.3% each by weight in the fermentation broth. In this embodiment, beads containing sodium lysocellin are produced with very little added base (see Example 2, below). Specifically, in this embodiment, it is sufficient to add the base in an amount which will raise the pH of the fermentation broth only to at least about 6.9, preferably within the range of 6.9 to about 7.2, at the beginning of the fermentation period and then maintain a pH of at least 6.9, and preferably within the range of 6.9 to 7.2, throughout the fermentation.

In a third embodiment, a cation salt of lysocellin is produced by adding mono-basic phosphates, such as sodium or potassium phosphates, such that the fermentation broth is buffered at pH 6.2 to 6.5 and then adding base, preferably at a concentration of about 20% w/w, to bring the pH to about 7.0 to about 7.2. This method allows bead formation at low phosphate concentration (see Example 3, below). Typically less than 0.3% by weight of the inorganic phosphate need be added to the broth to achieve the desired buffered pH. If a higher buffering pH is selected, for example, within the range of pH 6.8–6.9, the ions released by bringing the pH to pH 7.2 with base may not be sufficient to catalyze bead formation. Beads will form when the fermentation beer is buffered above pH 7.0 with mono- or di-basic phosphates, but only if sufficient base is added.

In addition to providing conditions such that the lysocellin will be produced in the form of a cationic salt, the presence of oil in the fermentation medium also contributes to the formation of lysocellin beads. Thus, lipids are provided to the fermentation broth both initially and as the fermentation progresses.

Examples of lipids which are suitable for use in this fermentation method include glyceride fats and oils commonly found in vegetable and animal oils. Free fatty acids typically do not directly contribute to bead formation.

An assimilable source of nitrogen also is provided in the culture medium. Suitable sources of nitrogen include yeast, yeast-derived products, enzyme-hydrolyzed caseine, peptones, cornmeal, soybean meal, cottonseed meal, amino acids such as glutamic acid and the like.

Nutrient inorganic salts also can be incorporated in the culture medium, such as soluble salts capable of yielding magnesium, calcium, ammonium, chloride, carbonate, sulfate, nitrate and like ions. Essential trace elements necessary for the growth and development of the microorganism also desirably are present in the culture medium. Such trace elements commonly occur as impurities in other constituents of the medium in amounts sufficient to meet the growth requirements of the organism.

The lysocellin is produced by growing the lysocellin-producing organism in an aerated, agitated, submerged culture. Fermentation generally can be carried out at slightly elevated temperatures, e.g., between about 25° C. and 32° C. Incubation of the broth desirably is carried out for a period of at least several days, typically between 4 and 12 days or longer if it is economically advantageous to do so.

It may be desirable to add small amounts (e.g., 0.2 ml/l) of an anti-foam agent, such as polypropylene glycol or a silicone polymer, to large-scale fermentation media if foaming becomes a problem. Excessive foaming can occur, for example, when fatty acids are added initially to the fermentation broth as the principal carbon source. If a combination of glycerides and free fatty acids are to be added to the fermentation broth, foaming can be controlled by holding the start of the glyceride/fatty acid addition until 16–18 hours post-inoculation. In addition, foaming can be controlled through careful regulation of physical parameters such as aeration, agitation or fermentor configuration (see Example 4, below).

In one embodiment, the lipid which combines with the lysocellin to form beads is comprised of glycerides. Suitable glycerides include soybean oil, safflower oil, cottonseed oil, sesame oil, olive oil, canola oil, rape oil, peanut oil, corn oil, sunflower oil and similar vegetable oils, cod oil and other fish oils, and lard and similar animal fat and oils. Vegetable oils are a preferred glyceride source, with soybean oil, canola oil and low palmitic soy oil being particularly preferred.

In a preferred embodiment of the invention, the fermentation broth contains as a principal carbon source glycerides or a mixture of free fatty acids and glycerides. Free fatty acids which can be used include saturated fatty acids such as lauric acid, myristic acid, palmitic acid, stearic acid, arachidic acid, lignoceric acid, and unsaturated fatty acids such as palmitoleic acid, oleic acid, linoleic acid linolenic acid and arachidonic acid. Unsaturated fatty acids are preferred, with oleic acid being most preferred. Desirably, the glyceride and free fatty acid are added to the fermentation medium at a rate of about 10–15 ml/liter/day, preferably at a rate of about 12 ml/liter/day.

In a particularly preferred embodiment, the fermentation broth contains as a principal carbon source a mixture of free fatty acids and glycerides, most preferably a mixture of oleic acid and soybean oil. Desirably, the weight:weight ratio of oleic acid to soybean oil is within the range of about 90:10 to 60:40, preferably 70:30, throughout the fermentation.

Free fatty acids, such as oleic acid, are much more quickly metabolized during fermentation in comparison to glyceride oils, but they generally are quite toxic to microorganisms except at low concentrations. Free fatty acids thus can be used advantageously to obtain higher lysocellin yields or titers by continuously feeding low concentrations of free fatty acids to the broth during fermentation at about a rate at which the free fatty acids are metabolized. If free fatty acids are used alone during fermentation as the principal carbon source and are depleted at the end of the fermentation, accruing crystals of the lysocellin are freely suspended in the fermentation broth and do not form beads. Addition of a combination of glycerides and free fatty acids during fermentation, which preferably are fed on a continuous basis to the on-going fermentation, will facilitate the formation of beads.

In a preferred embodiment, the fermentation broth initially contains as a principal carbon source from about 1% to about 10% (preferably 1–5%, more preferably 2–3%) by weight glycerides, such as soybean oil. Free fatty acids, such as oleic acid, mixed with oil, are fed to the fermentation broth at a rate of 5–15 g/l/day. This feed rate is sufficient to provide free fatty acids during fermentation in which a lysocellin titer in excess of about 20 g/l is achieved. In addition to its role as a supplemental nutrient, the oil provided in the mixed feed acts to bind the salt form of lysocellin to the bead.

Advantageously, the free fatty acids are fed to the broth in combination with glycerides during fermentation. The free fatty acids and glycerides are fed to the broth during fermentation until the desired concentration of lysocellin in the fermentation broth is achieved, generally in about 10–12 days.

At the end of the fermentation, e.g., during the last 24 hours of fermentation, if excess glycerides are present in the broth, glyceride addition to the broth is terminated until a desired amount of glycerides have been metabolized. Using the method of the present invention, in excess of 75%, and as much as 90–95%, of the total fermentor lysocellin can be reproducibly produced in bead form with high purity. The resulting beads can be separated from the fermentation broth by screening as noted above. The beads are of high purity, containing at least 50–75% lysocellin cation salt (e.g., sodium lysocellin) by weight and only trace amounts of other cations (e.g., potassium and calcium).

The recovered beads then can be treated in accordance with conventional processing to obtain the desired lysocellin. Such methods are described, for example, in U.S. Pat. No. 5,047,338, incorporated herein by reference. This simple method of recovery from beads obviates the need for complicated and expensive multi-stage extractions and related filtration, chromatography, concentration and crystallization operations normally required for the recovery of hydrophobic antibiotics such as polyethers.

The invention is illustrated by the following examples which are not intended to be limiting.

duced beginning at inoculation in a semi-continuous feed (~12 ml/l/day).

The physical parameters using a 12 liter New Brunswick Microgen fermentor were as follows:

| | |
|---|---|
| Temperature | 30° C. +/− 1° C. |
| Air | 8 l/min. |
| Pressure | 2 PSI g |
| Agitation | 1 impeller (4" Rushton disk) 590–605 rpm |

Condenser in place to reduce evaporation loss.

Beads formed consistently when fermentor pH was maintained at pH 7.2 or above. When beads formed, small (<3 mM), soft, irregular shaped globs containing lysocellin and oil were observed on days 3 & 4. By day 5 these beads had aggregated, hardened, and were spherical in shape. At harvest on day 12, the beads were collected by pouring the beer through an 18 or 30 mesh screen. All the bead lysocellin was in the salt form. Since the caustic was the primary source of cation in the fermentor, the lysocellin salt directly correlated with the cation of the caustic (Table 1).

TABLE I

| Batch No. | pH Setpoint | Caustic | Equi. vol.[a] | Maint. vol.[b] | % lyc in bead[c] | bead lyc cont. (%)[d] | bead size | salt of lysocellin |
|---|---|---|---|---|---|---|---|---|
| 1 | pH 6.6 | 20% Sodium Hydroxide | 0 ml | 11–17 ml | 0.0 | — | none | no salt |
| 2 | pH 6.9 | 20% Sodium Hydroxide | 10 ml | 15–25 ml | 0.0 | — | none | no salt |
| 3 | pH 7.2 | 20% Sodium Hydroxide | 10 ml | 15–25 ml | 78.8 | 53.9 | 5–7 mm | Sodium |
| 4 | pH 7.6 | 20% Sodium Hydroxide | 8 ml | 20–25 ml | 90.0 | 56.9 | 5–7 mm | Sodium |
| 5 | pH 7.2 | 20% Potas. Hydroxide | 20 ml | 25–40 ml | 75.0 | 71.9 | 1–3 mm | Potassium |

[a]Volume caustic required to bring initial fermentor pH to pH setpoint.
[b]Volume caustic required daily to maintain fermentor pH at pH setpoint.
[c]Percent of total fermentor lysocellin contained in bead form.
[d]Content of beads which were isolated which is lysocellin (in percent).

Example I

INOCULUM

A 500 ml flask containing GPB first stage inoculum medium (by wt.: 2% glycerol, 1% Bacto Peptone, 1% Bacto Meat Extract and tap water to volume) was inoculated with one ml of lysocellin producing *Streptomyces cacaoi* var. *asoensis* seed culture (stored at −80° C.) and incubated on a rotary shaker at 28°–30° C., for 22–30 hr. 2.5–3.0 ml of mature GPB seed culture was added to 100 ml 22A media [2.5% soy flour, 2.5% soy oil, 0.15% $KH_2PO_4$—$H_2O$, 0.15% $K_2HPO_4$ and trace elements (final conc.: 50 ppm $FeSO_4$, 15 ppm $MnSO_4$—$H_2O$, 20 ppm $CoCl_2$—$6H_2O$, and 30 ppm $H_2SO_4$)] in a 500 ml flask and incubated on a rotary shaker at 28°–30° C., for 22–26 hr. The second stage seed was directly transferred to the fermentor.

FERMENTATION AT pH 7.2

Fermentation production medium [4.5% soy flour, 3% soy oil, 0.05% $KH_2PO_4$—$H_2O$, 0.15% $K_2HPO_4$, trace elements (as above) and 2 ml Sigma Type A antifoam] was prepared to 8 liter volume and sterilized in-place. The pH of the medium was adjusted to the pH setpoint prior to inoculation and maintained throughout the fermentation with 20% caustic. The fermentor was inoculated with 200 ml of mature second stage seed and oleic acid:soy oil (70:30) was intro-

EXAMPLE II

FERMENTATION WITH $NaPO_4$ BUFFER 8 l of production medium [4.5% soy flour, 3% soy oil, 0.3% $NaH_2PO_4$—$H_2O$, 0.3% $Na_2HPO_4$, trace elements (as in example I), and 2 ml Sigma Type A antifoam] were prepared and sterilized in-place. Physical parameters, inoculation and oil feeding were as in Example I. The buffered pH of the medium (6.8) was adjusted to pH 6.9 prior to inoculation with 3 ml 20% NaOH. The medium was maintained at pH 6.9 throughout the fermentation with 20% NaOH.

Only 24 ml of caustic were required to maintain 6.9 pH for the first 64 hours (11–22 ml/day thereafter). Therefore, at the time of initial bead formation the primary source of cations in the fermentation beer was the inorganic $NaPO_4$ buffer. At harvest on day 12, the 5–8 mm beads were collected by pouring the beer through an 18 mesh screen. The beads were 64% lysocellin by weight in the sodium salt form. Approximately 77% of the total lysocellin produced in the fermentor was contained in the beads.

EXAMPLE III

FERMENTATION WITH $NaH_2PO_4$ 8 l of production medium [4.5% soy flour, 3% soy oil, 0.2% $NaH_2PO_4$—$H_2O$, trace elements (as in example I), and 2 ml Sigma Tripe A antifoam] were prepared and sterilized in-place. Physical parameters and inoculation were as in Example I and oil feed was initiated at 16.5 hr post inoculation. The buffered pH of the medium (6.2) was adjusted to pH 7.2 prior to inoculation with 16 ml 20% NaOH. The media was maintained at pH 7.2 throughout the fermentation with 20% NaOH.

In order to maintain 7.2 pH throughout the fermentation 12–22 ml of 20% NaOH was required each day. At harvest on day 12, the 3–12 mm beads were collected by pouring the beer through an 18 mesh screen. The beads were 56% lysocellin by weight in the sodium salt form. Approximately 91% of the total lysocellin produced in the fermentor was contained in the beads. This example demonstrates bead formation with low phosphate concentration.

EXAMPLE IV

HIGH VOLUME BEAD FERMENTATION 12 l of production medium ingredients [4.5% soy flour, 3% soy oil, 0.15% $NaH_2PO_4$, trace elements (as in example I) and antifoam (7.5 ml Mazu 37-C & 2.5 ml Mazu DF100S)] were prepared in 10 l of water and sterilized in-place. Following sterilization, 1 l of sterile water was added and the pH of the medium was adjusted to pH 7.2 with 22 ml 20% NaOH. The fermentor was inoculated with 300 ml inoculum prepared as in Example I except the medium contained $NaPO_4$'s in place of $KPO_4$'s. Oleic acid:soy oil (70:30) feed was started (~12ml/l/day) and a second liter of sterile water was added at 16 hr post inoculum. The media was maintained at pH 7.2 throughout the fermentation with 20% NaOH.

Physical parameters using a 12 l New Brunswick Microgen fermentor were as follows (Note—air and agitation were modified to control foaming):

Temperature
  30°±1° C.
Air
  10 l/min 0–42 hr
  13.5 l/min. after 42 hr
Pressure
  2 PSI g
Agitation
  2 impellers (4¼" hydrofoil)
  400±2 rpm 0–16 hr
  500±2 rpm 16–42 hr
  600±2 rpm 42 hr-end For the first two days, the pH remained at or above pH 7.2 with little added caustic (8 ml through 48 hr). In order to maintain 7.2 pH throughout the remainder of the fermentation 25–42 ml of 20% NaOH was required each day. At harvest on day 12, the 4–5 mm beads were collected by pouring the beer through an 18 mesh screen. The beads were 63% lysocellin by weight in the sodium salt form. Approximately 94% of the total lysocellin produced in the fermentor was contained in the beads. This example demonstrates bead formation with low phosphate concentration and control of foaming at maximal fermentor volume.

We claim:

1. A method for producing lysocellin in bead form which comprises the steps of:
  (a) cultivating a lysocellin-producing microorganism in an aqueous nutrient-containing fermentation broth under lysocellin-producing conditions so as to produce lysocellin;
  (b) adding a precalculated amount of base or inorganic salt to said fermentation broth so as to provide said fermentation broth with a concentration of base or salt of at least about 25 mM within the first 24 hours from the beginning of fermentation such that said lysocellin is in the form of a cation salt;
  (c) providing a lipid to said fermentation broth such that throughout the fermentation said lipid is present in said fermentation broth in an amount which is sufficient to form discrete beads with said cation salt of lysocellin in said fermentation broth; and
  (d) separating said beads from said fermentation broth.

2. The method of claim 1, wherein the base comprises sodium hydroxide, mono- or di-basic sodium phosphate, potassium hydroxide, mono- or di-basic potassium phosphate, mono- or di-basic ammonium phosphate or ammonium hydroxide.

3. The method of claim 2, wherein the base or inorganic salt comprises sodium hydroxide or mono- or di-basic sodium phosphate.

4. The method of claim 1, wherein the base or inorganic salt is added to a concentration of about 25 mM to about 50 mM.

5. The method of claim 1, wherein the base or inorganic salt is added to the fermentation broth in an amount sufficient to raise the pH of the fermentation broth to at least 7.2 and to maintain the pH at at least 7.2 throughout the fermentation.

6. The method of claim 5, wherein the pH of the fermentation broth is maintained within the range of about 7.2 to about 7.6.

7. The method of claim 1, wherein the fermentation broth comprises mono- and di-valent inorganic phosphate salts at a concentration of at least 0.3% each and sufficient base or organic salt is added to the fermentation broth prior to and after inoculation with the microorganism to raise and maintain the pH of the fermentation broth to at least about 6.9.

8. The method of claim 7, wherein the pH of the fermentation broth is maintained within the range of about 6.9 and 7.2.

9. The method of claim 1, wherein the fermentation broth is buffered with monobasic inorganic phosphates at a pH within the range of about 6.2 to about 6.5 and base is added to the broth prior to and after inoculation with the microorganism in an amount sufficient to raise and maintain the pH of the broth to at least about 7.0.

10. The method of claim 9, wherein the pH of the fermentation broth is maintained within the range of about 7.0 and about 7.6.

11. The method of claim 1, wherein the lipid comprises glycerides, fatty acids, phospholipids or mixtures thereof.

12. The method of claim 1, wherein the fermentation broth comprises as the principal carbon source glycerides, free fatty acids or a mixture thereof.

13. The method of claim 12, wherein the fermentation broth comprises as the principal carbon source a mixture of free fatty acids and glycerides.

14. The method of claim 13, wherein the glycerides are present in soybean oil and the fermentation broth contains as the principal carbon source a mixture of oleic acid and soybean oil.

15. The method of claim 14, wherein the weight:weight ratio of oleic acid to soybean oil is within the range of about 60:40 to about 90:10.

16. The method of claim 15, wherein the weight:weight ratio of oleic acid to soybean oil is about 70:30.

* * * * *